United States Patent
Suzuki et al.

(10) Patent No.: US 10,852,300 B2
(45) Date of Patent: Dec. 1, 2020

(54) **IMMUNOCHROMATOGRAPHIC ANALYZER FOR *MYCOPLASMA PNEUMONIAE* DETECTION**

(71) Applicant: TANAKA KIKINZOKU KOGYO K.K., Tokyo (JP)

(72) Inventors: Keita Suzuki, Hiratsuka (JP); Hisahiko Iwamoto, Hiratsuka (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 41 days.

(21) Appl. No.: 15/578,493

(22) PCT Filed: Jun. 1, 2016

(86) PCT No.: PCT/JP2016/066310
§ 371 (c)(1),
(2) Date: Nov. 30, 2017

(87) PCT Pub. No.: WO2016/194986
PCT Pub. Date: Dec. 8, 2016

(65) Prior Publication Data
US 2018/0172684 A1    Jun. 21, 2018

(30) Foreign Application Priority Data

Jun. 1, 2015 (JP) ................................ 2015-111732
Aug. 31, 2015 (JP) ................................ 2015-171163

(51) Int. Cl.
| | |
|---|---|
| G01N 33/554 | (2006.01) |
| G01N 33/569 | (2006.01) |
| C07K 14/30 | (2006.01) |
| G01N 33/543 | (2006.01) |
| G01N 33/531 | (2006.01) |

(52) U.S. Cl.
CPC ....... *G01N 33/56933* (2013.01); *C07K 14/30* (2013.01); *G01N 33/531* (2013.01); *G01N 33/543* (2013.01); *G01N 33/569* (2013.01)

(58) Field of Classification Search
None
See application file for complete search history.

(56) References Cited

U.S. PATENT DOCUMENTS

| | | |
|---|---|---|
| 7,776,542 B1 | 8/2010 | Aoyagi et al. |
| 2011/0097818 A1 | 4/2011 | Itoh |
| 2011/0262892 A1 | 10/2011 | Aoyagi et al. |
| 2013/0137192 A1 | 5/2013 | Iwamoto et al. |
| 2013/0171740 A1 | 7/2013 | Sakakibara |
| 2016/0202257 A1 * | 7/2016 | Saito ................. C07K 16/1253 435/7.32 |
| 2017/0242007 A1 * | 8/2017 | Tomiyama ............... C12N 5/10 |
| 2018/0009880 A1 | 1/2018 | Saito |

FOREIGN PATENT DOCUMENTS

| | | | |
|---|---|---|---|
| CN | 104198703 A | 12/2014 | |
| JP | 61-274687 A | 12/1986 | |
| JP | S62-192661 A | 8/1987 | |
| JP | S62-192662 A | 8/1987 | |
| JP | H07-046104 B2 | 5/1995 | |
| JP | H11-108932 A | 4/1999 | |
| JP | 2004-189665 A | 7/2004 | |
| JP | 2005-291780 A | 10/2005 | |
| JP | 2007-163182 A | 6/2007 | |
| JP | 2009-085911 A | 4/2009 | |
| JP | 2010-019786 A | 1/2010 | |
| JP | 2010-19796 * | 1/2010 | ........... G01N 33/543 |
| JP | 2010-19796 A | 1/2010 | |
| JP | 2011-209140 A | 10/2011 | |
| JP | 2012-037253 A | 2/2012 | |
| JP | 2012-058058 A | 3/2012 | |
| JP | 2012-159440 A | 8/2012 | |
| JP | 2013-072663 A | 4/2013 | |
| JP | 2014-167439 A | 9/2014 | |
| WO | WO 2011/125606 A1 | 10/2011 | |
| WO | WO 2015/025968 A1 | 2/2015 | |
| WO | WO-2015025968 A1 * | 2/2015 | ........... G01N 33/569 |
| WO | WO 2016/017598 A1 | 2/2016 | |
| WO | WO 2016-121831 A1 | 8/2016 | |

OTHER PUBLICATIONS

Chang et al. J.Bacteriology vol. 193, No. 7, pp. 1726-1733, 2011 (Year: 2011).*
EP, Extended European Search Report for European patent Application No. 16803420.5, dated Feb. 5, 2018.
Layh-Schmitt et al., "The adhesin related 30-kDa protein of Mycoplasma pneumoniae exhibits size and antigen variability", FEMS Microbiol Lett, Jan. 1, 1997, pp. 101-108.
Varshney et al., "Cloning, Expression, and Immunological Characterization of the P30 Protein of Mycoplasma pneumoniae", Clinical and Vaccine Immunology, vol. 15, No. 2, Feb. 1, 2008, pp. 215-220.
Montagnani et al. "Use of recombinant chimeric antigens for the serodiagnosis of Mycoplasma pneumoniae infection", European Journal of Clinical Microbiology & Infectious Diseases, Springer, Berlin, DE, vol. 29, No. 11, Jul. 15, 2010, pp. 1377-1386.

(Continued)

*Primary Examiner* — Jana A Hines
*Assistant Examiner* — Khatol S Shahnan Shah
(74) *Attorney, Agent, or Firm* — Orrick, Herrington & Sutcliffe LLP; Joseph A. Calvaruso; K. Patrick Herman

(57) ABSTRACT

The present invention is intended to provide an immunochromatographic analyzer that enables a quick and easy, high-sensitivity detection of *Mycoplasma pneumoniae*, and thus more reliable and faster diagnosis of *mycoplasma* pneumonia. The immunochromatographic analyzer according to the present invention is for detecting *Mycoplasma pneumoniae*, and includes a sample adding section, a label-substance retaining section, a chromatographic medium section having a detection section, and an absorbing section. The label-substance retaining section and the detection section contain an antibody that strongly recognizes domain III of P30 protein of *Mycoplasma pneumoniae* consisting of the amino acid sequence of SEQ ID NO: 2.

4 Claims, 3 Drawing Sheets
Specification includes a Sequence Listing.

(56) References Cited

OTHER PUBLICATIONS

JP, Priority document—Japanese Application No. 2015-015253, Jan. 29, 2015.
JP, Notice of Opposition—01 2015-171163, Japanese Patent No. 6143818, Pat Opposition No. 2017-701151 (Itou, Masaya), Feb. 14, 2018.
JP, Notice of Opposition—02 2015-171163, Japanese Patent No. 6143818, Pat Opposition No. 2017-701151 (Itou, Masaya), Feb. 14, 2018.
JP, Reasons for Revocation 2015-171163, Japanese Patent No. 6143818, Pat Opposition No. 2017-701151 (Itou, Masaya), Mar. 9, 2018.
Dallo, et al., "Biofunctional Domains of the Mycoplasma pneumoniae P30 Adhesin", Infection and Immunity, vol. 64, No. 7, Jul. 1996 p. 2595-2601.
JP, Correction Request for Opposition No. 2017-701151 (U.S. Pat. No. 6,143,818), May 8, 2018.
JP, Written Opinion for Opposition No. 2017/701151 (U.S. Pat. No. 6,143,818), dated May 8, 2018.
JP, Written Statement for Opposition No. 2017-701151 (U.S. Pat. No. 6,143,818), dated Jun. 6, 2018.
JP, Correction Request for Opposition No. 2017-701151 (U.S. Pat. No. 6,143,818), Oct. 26, 2018.
JP, Written Opinion for Opposition No. 2017/701151 (U.S. Pat. No. 6,143,818), dated Oct. 26, 2018.
JP, Notification of Reasons for Revocation for Patent Opposition No. 2017/701151 (U.S. Pat. No. 6,143,818), dated Aug. 27, 2018.
JP, Notification of Sending a Duplicate of Written Opinion for Patent Opposition No. 2017/701151 (U.S. Pat. No. 6,143,818), dated Aug. 27, 2018.
PCT, International Search Report for PCT/JP2016/066310, dated Aug. 16, 2016.
Chang et al., Domain Analysis of Protein P30 in Mycoplasma Pneumoniae Cytadherence and Gliding Motility, Journal of Bacteriology Apr. 2011, vol. 193, No. 7, p. 1726-1733.
Beghetto et al., Discovery of new Mycoplasma Pneumoniae Antigens by Use of a Whole-Genome Lambda Display Library, Institut Pasteur, Microbes and Infection, 2009, 11 (1), 66-73.

* cited by examiner

[Fig. 1]
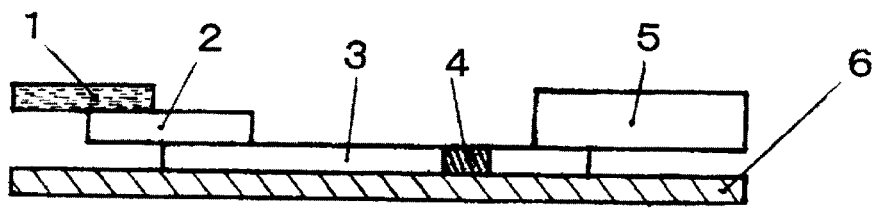
[Fig. 2]
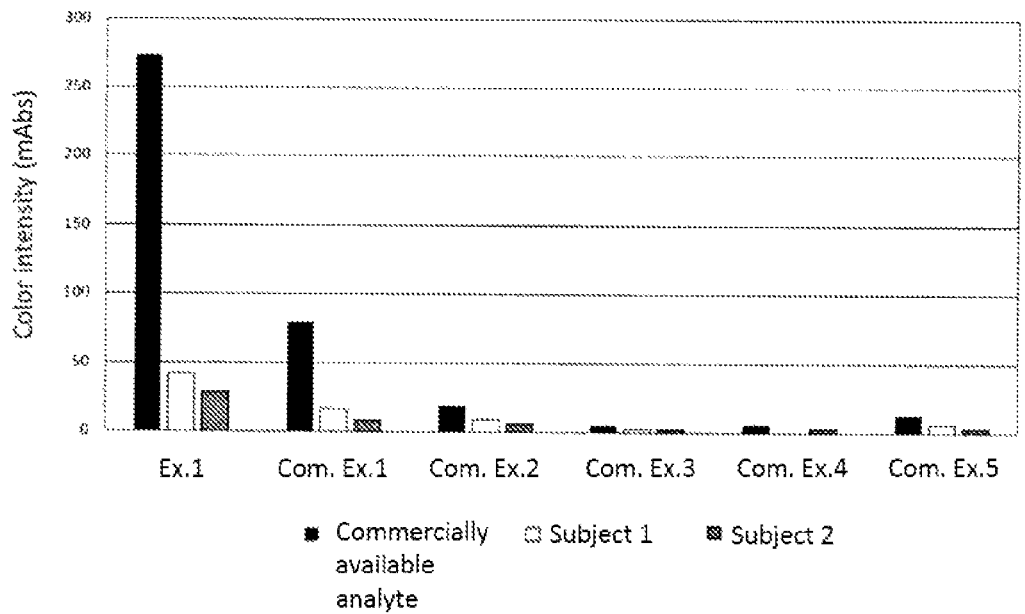
[Fig. 3]
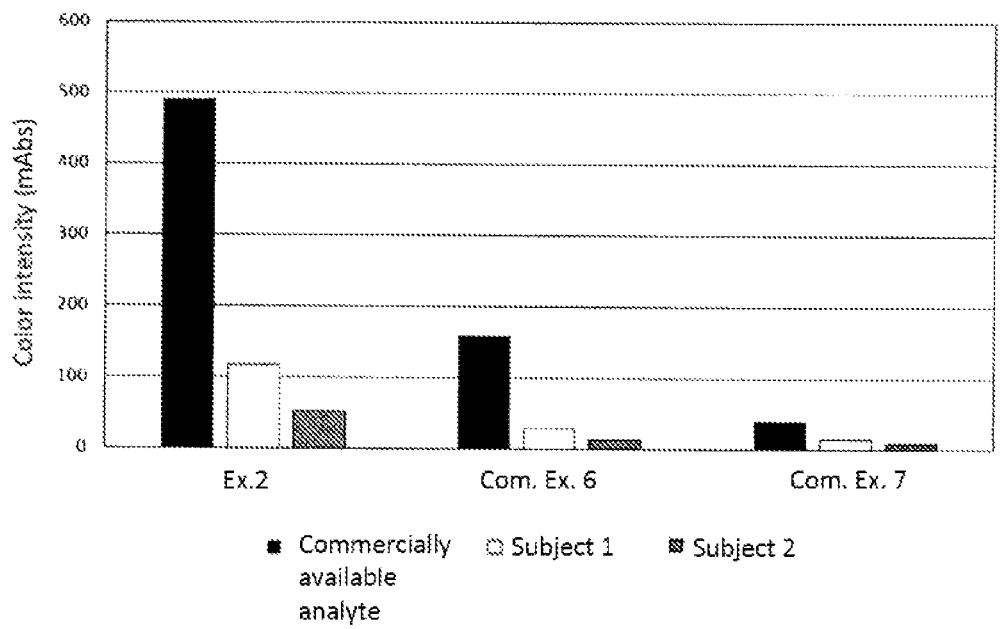

[Fig.4]
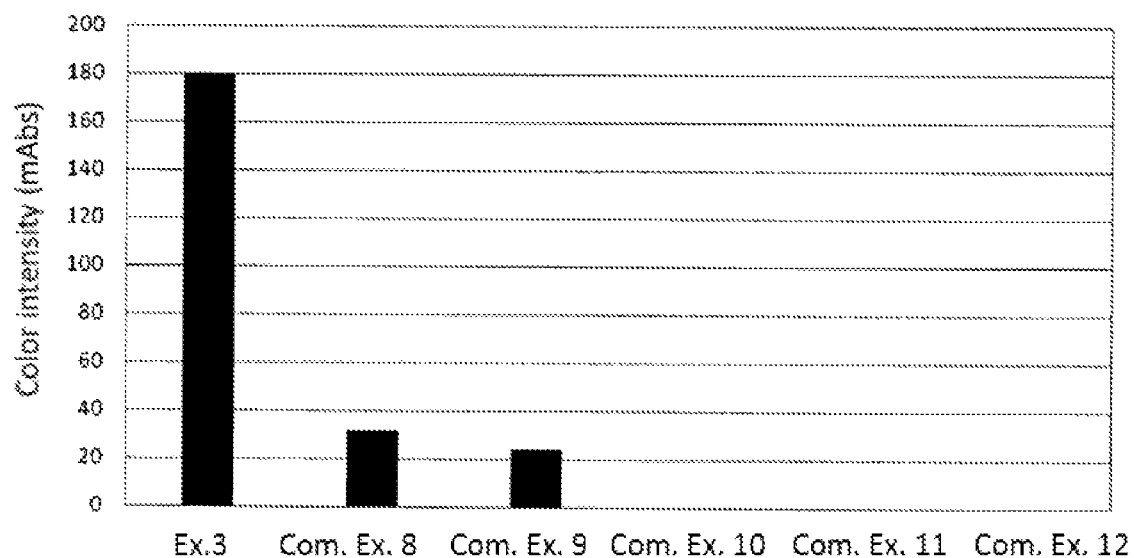
[Fig. 5]
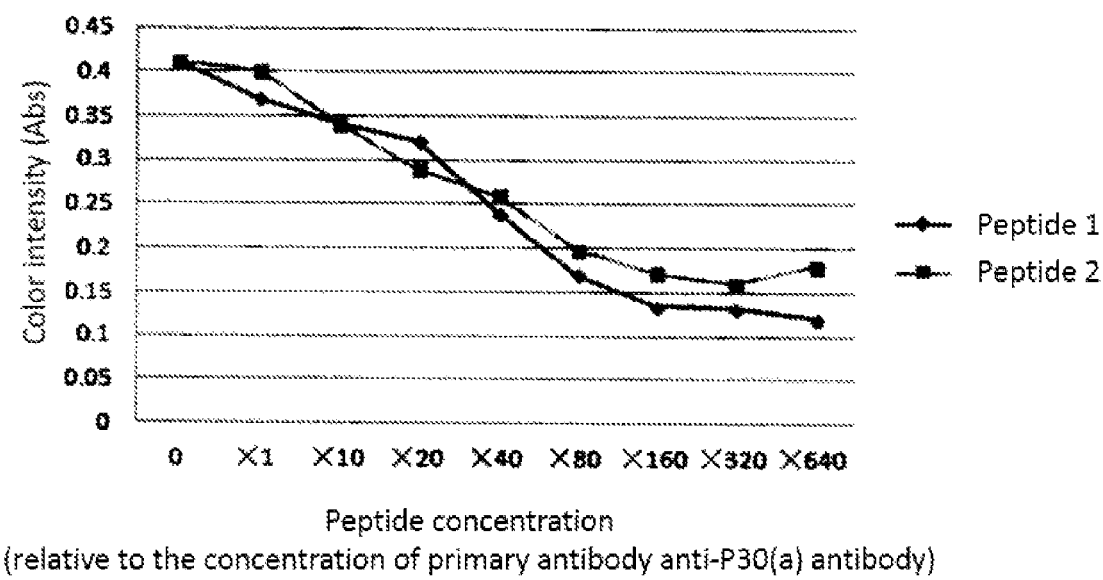
Peptide concentration
(relative to the concentration of primary antibody anti-P30(a) antibody)

[Fig. 6]
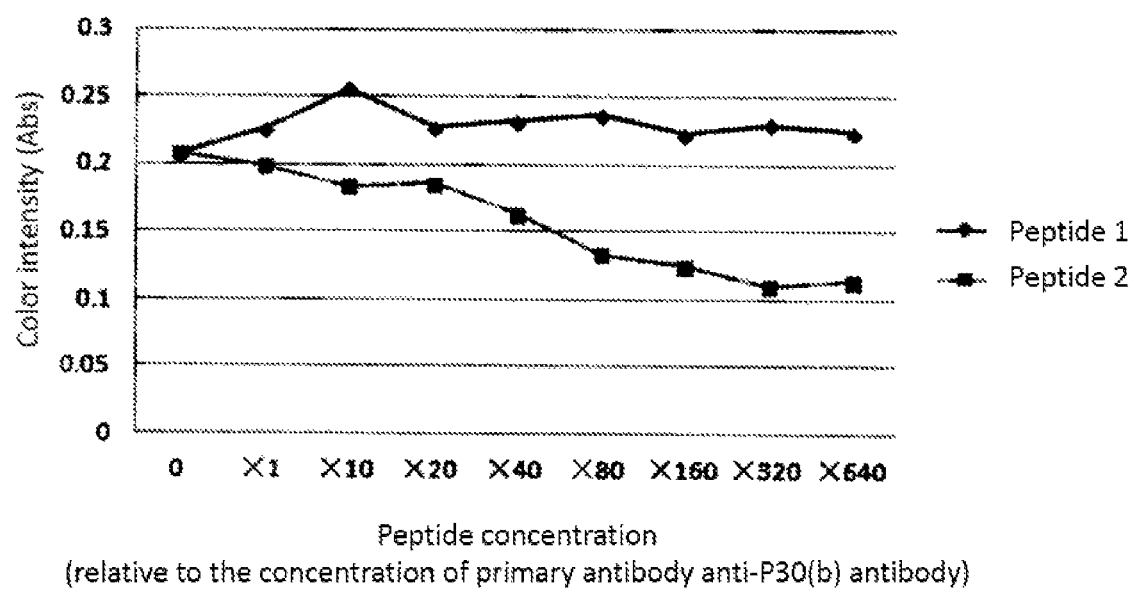

IMMUNOCHROMATOGRAPHIC ANALYZER FOR *MYCOPLASMA PNEUMONIAE* DETECTION

TECHNICAL FIELD

The present invention relates to an immunochromatographic analyzer for detecting *Mycoplasma pneumoniae*, and to an immunochromatographic analysis kit, and a method for detecting *Mycoplasma pneumoniae*.

BACKGROUND ART

*Mycoplasma* pneumonia is a respiratory infection caused primarily by *Mycoplasma pneumoniae*. *Mycoplasma pneumoniae* is a typical causative bacterium of atypical pneumonia. The typical age groups affected by *mycoplasma* pneumonia are infants, schoolchildren, and adolescence (aged between 5 and 35). Early symptoms include symptoms that resemble a cold syndrome, or cold-like symptoms as they are often called. These symptoms involve episodes of coughing that aggravate with time, and may persist for as long as about a month even after fever has subsided.

A variety of methods are available for diagnosis of *mycoplasma* pneumonia. For example, detection methods are available that use antibodies against *Mycoplasma pneumoniae*. For antibiotics selection, there is a strong need in the clinic to determine the presence or absence of a *Mycoplasma pneumoniae* infection in early stages of *mycoplasma* pneumonia infection. A quick and easy detection of *Mycoplasma pneumoniae* for diagnosis of *mycoplasma* pneumonia is possible by applying such methods to the easy-to-operate, immunochromatographic analysis technique.

An immunochromatographic analyzer used for the immunochromatographic analysis technique has a structure, which in its simplest form, includes a sample adding section, a label-substance retaining section, a chromatographic medium section having a detection section and an absorbing section, which are interconnected to each other.

For example, patent document 1 discloses an immunochromatographic analyzer that uses a monoclonal antibody specific to P1 protein of *Mycoplasma pneumoniae*.

Patent document 2 discloses an immunochromatographic analyzer that uses an antibody specific to ribosomal protein L7/L12 of *Mycoplasma pneumoniae*.

RELATED ART

Patent Document

Patent document 1: JP-A-2013-72663
Patent document 2: JP-A-2014-167439

DISCLOSURE OF INVENTION

Technical Problem

However, the traditional diagnosis methods using immunochromatographic analyzers that use antibodies against *Mycoplasma pneumoniae* are not sensitive enough for *Mycoplasma pneumoniae*, and involve many non-specific reactions. The methods are therefore not sufficient for diagnosis of *Mycoplasma pneumoniae* infections.

The present inventors conducted extensive studies, and, by focusing on P30 protein of *Mycoplasma pneumoniae* as a potential target protein that enables a more sensitive detection than P1 protein of *Mycoplasma pneumoniae*, found that a high-sensitive detection of *Mycoplasma pneumoniae* is possible with an antibody that recognizes a specific site of P30 protein.

It was also found that a quick and easy, high-sensitive detection of *Mycoplasma pneumoniae* infection is possible with an immunochromatographic analyzer that uses an antibody that binds to a specific site of P30 protein of *Mycoplasma pneumoniae*. The present invention has been completed on the basis of these findings.

Means for Solving the Problems

The present invention is as follows.

1. An immunochromatographic analyzer for detecting *Mycoplasma pneumoniae*, comprising: a sample adding section; a label-substance retaining section; a chromatographic medium section having a detection section; and an absorbing section, wherein the label-substance retaining section and the detection section contain an antibody that strongly recognizes domain III of P30 protein of *Mycoplasma pneumoniae* consisting of the amino acid sequence of SEQ ID NO: 2.
2. The immunochromatographic analyzer according to above 1, wherein the antibody recognizes the amino acid sequence of SEQ ID NO: 3 in the domain III.
3. The immunochromatographic analyzer according to above 1 or 2, wherein the label substance contained in the label-substance retaining section is a gold particle, and the label-substance retaining section contains the gold particle in an amount of 0.25 to 0.7 μg/cm$^2$.
4. An immunochromatographic analysis kit comprising: the immunochromatographic analyzer of any one of above 1 to 3; and an analyte diluting solution for diluting and developing an analyte.
5. The immunochromatographic analysis kit according to above 4, wherein the analyte diluting solution contains at least one type of non-ionic surfactant.
6. The immunochromatographic analysis kit according to above 5, wherein at least 50% of the non-ionic surfactant contained in the analyte diluting solution is a non-ionic surfactant having an HLB value of 13 to 18.
7. A method for detecting *Mycoplasma pneumoniae* in an analyte using an immunochromatographic analyzer that includes a sample adding section, a label-substance retaining section, a chromatographic medium section having a detection section and an absorbing section, the method comprising the steps of: (1) adding to the sample adding section an analyte-containing solution prepared by diluting the analyte with an analyte diluting solution; (2) recognizing *Mycoplasma pneumoniae* with an antibody (hereinafter, "antibody P30(A)") that is retained in the label-substance retaining section, and that strongly recognizes domain III of P30 protein of *Mycoplasma pneumoniae* consisting of the amino acid sequence of SEQ ID NO: 2; (3) developing the analyte and the antibody P30(A) as a mobile phase through the chromatographic medium section; and (4) detecting the *Mycoplasma pneumoniae* in the mobile phase developed, using the antibody P30(A) contained in the detection section.

Effects of Invention

The present invention enables a quick and easy, high-sensitive detection of *Mycoplasma pneumoniae* with an immunochromatographic analyzer that uses an antibody that binds to a specific site of P30 protein of *Mycoplasma*

*pneumoniae*. That is, the present invention enables a reliable and quick diagnosis of *mycoplasma* pneumonia.

BRIEF DESCRIPTION OF DRAWINGS

FIG. 1 is a cross sectional view showing the structure of an immunochromatographic analyzer of an embodiment of the present invention.

FIG. 2 is a graph representing the results of color intensity measurements in the detection of *Mycoplasma pneumoniae* conducted with the immunochromatographic analyzer of the present invention.

FIG. 3 is a graph representing the results of color intensity measurements in the detection of *Mycoplasma pneumoniae* conducted with the immunochromatographic analyzer of the present invention.

FIG. 4 is a graph representing the results of color intensity measurements in the detection of P30 protein of *Mycoplasma pneumoniae* conducted with the immunochromatographic analyzer of the present invention.

FIG. 5 is a graph representing the results of color intensity measurements in a competitive inhibition ELISA conducted in Test Example 4 with antibody P30(a) using the peptide 1 or 2 as an antigen.

FIG. 6 is a graph representing the results of color intensity measurements in a competitive inhibition ELISA conducted in Test Example 4 with antibody P30(b) using the peptide 1 or 2 as an antigen.

EMBODIMENTS FOR CARRYING OUT THE INVENTION

An embodiment for carrying out the present invention is described below.

An immunochromatographic analyzer for detecting *Mycoplasma pneumoniae* of the present invention includes a sample adding section where an analyte is added, a label-substance retaining section for retaining a label substance, a chromatographic medium section having a detection section where *Mycoplasma pneumoniae* is detected, and an absorbing section for absorbing the liquid that has passed the detection section. The label-substance retaining section and the detection section contain an antibody that strongly recognizes domain III of P30 protein of *Mycoplasma pneumoniae*.

The antibody used for the immunochromatographic analyzer of the present invention is an antibody that strongly recognizes domain III of P30 protein of *Mycoplasma pneumoniae* (hereinafter, also referred to as "antibody P30(A)").

The P30 protein of *Mycoplasma pneumoniae* is a proline-rich (20.7%) adhesion protein consisting of the 274 amino acids represented by SEQ ID NO: 1, and having a molecular weight of 29,743.

The domain III of P30 protein is represented by SEQ ID NO: 2, and it is a region corresponding to positions 177 to 274 of the amino acid sequence of P30 protein (SEQ ID NO: 1), and this domain is rich in repeating sequences of specific amino acids. Domain III has three different amino-acid repeating sequences, which include seven occurrences of the amino acid sequence represented by SEQ ID NO: 3 (PGMAPR), three occurrences of the amino acid sequence represented by SEQ ID NO: 4 (PGMPPH), and three occurrences of the amino acid sequence represented by SEQ ID NO: 5 (PGFPPQ).

The antibody P30(A) used in the present invention recognizes the domain III that is rich in these amino-acid repeating sequences, and exhibits a notable effect by greatly improving detection sensitivity, presumably by forming the sandwich structure below in an analysis using the immunochromatographic analyzer of the present invention.

Specifically, with the label-substance retaining section and the detection section containing the antibody P30(A) in the immunochromatographic analyzer of the present invention, the antibody P30(A) retained in the label-substance retaining section binds to a part of the repeating sequences in domain III of P30 protein of *Mycoplasma pneumoniae*.

The antibody P30(A) immobilized in the detection section then binds to the same repeating sequence but at a different position from the sequence that has bound to the antibody P30(A) retained in the label-substance retaining section. In this way, these two antibodies P30(A) form a sandwich structure on the both sides of the P30 protein, and enable detection of *Mycoplasma pneumoniae*.

In this manner, the antibody P30(A) recognizes the domain III having the foregoing repeating sequences. By recognizing multiple locations of P30 protein, the antibody P30(A) appears to improve the detection sensitivity to *Mycoplasma pneumoniae*.

Preferably, the antibody P30(A) used in the present invention recognizes at least the amino acid sequence of SEQ ID NO: 3 (PGMAPR) in the amino-acid repeating sequences of domain III. The antibody more strongly recognizes domain III of P30 protein of *Mycoplasma pneumoniae* by recognizing this sequence, and enables high-sensitive detection of *Mycoplasma pneumoniae*, as is described in the results of Examples below.

The antibody P30(A) of the present invention "strongly recognizing domain III of P30 protein of *Mycoplasma pneumoniae*" is defined as an antibody that produces an absorbance of 0.2 Abs or more at 450 nm in an ELISA test.

Specifically, an ELISA is conducted according to the following protocol. First, 100 μL of 4 ng/mL of *mycoplasma* pneumonia P30 (purified protein P30Ag produced by expressing amino acids 96-274 with *Escherichia coli* using an ordinary method) in 50 mM carbonate buffer (pH 9.5) is added to a 96-well ELISA plate Nunc Immuno modules (Thermo Fisher Scientific, Code 469949), and incubated at 4° C. for 16 hours. After the 16-hour incubation period, the P30 solution is removed, and the wells are washed three times with 300 μL of PBST (0.05% Tween 20 in PBS). The remaining solution in the wells is removed by tapping the plate against a paper towel.

Three-hundred microliters of a 5% BSA in PBST (BSA; Oriental Yeast Co., Ltd.) is added as a blocking solution, and incubated at 37° C. for 1 hour. After that, the BSA solution is removed, and the wells are washed three times with 300 μL of PBST (0.05% Tween 20 in PBS). The remaining solution in the wells is removed by tapping the plate against a paper towel.

One-hundred microliters of 5 μg/mL of an anti-*Mycoplasma pneumoniae* P30 antibody (antibody P30(A)) in 50% blocking solution is added as primary antibody to the wells, and incubated at 37° C. for 1 hour. After that, the primary antibody solution is removed, and the wells are washed three times with 300 μL of PBST (0.05% Tween 20 in PBS).

One-hundred microliters of 1 mg/mL of Anti Mouse IgG (H+L), Rabbit, IgG Whole, Peroxidase Cojugated (Wako Pure Chemical Industries, Ltd.; Code 014-17611) is added as secondary antibody to the wells, and incubated at 37° C. for 1.5 hours. After that, the BSA solution is removed, and the wells are washed three times with 300 μL of PBST (0.05% Tween 20 in PBS). The remaining solution in the wells is removed by tapping the plate against a paper towel.

One-hundred microliters of a chromogenic substrate Sure Blue Reserve TMB Microwell Peroxidase Substrate (1-Component; KPL; Code 53-00-01) is added as a chromogenic substrate to the wells. A reaction is allowed for 15 minutes, and quenched by adding 100 µL of 2 N sulfuric acid.

Absorbance at 450 nm is measured using a microplate reader (BIORAD).

An antibody that produced a measured absorbance of 0.2 Abs or more according to the foregoing method after subtracting the absorbance of a blank (wells that underwent a chromogenic reaction with the secondary antibody without the primary antibody) was selected as the antibody that "strongly recognizes domain III of P30 protein of *Mycoplasma pneumoniae*".

The antibody P30(A) of the present invention "strongly recognizing domain III of P30 protein of *Mycoplasma pneumoniae*" also can be more specifically defined as an antibody that reacts with protein A (full-length *mycoplasma* pneumonia P30 protein; amino acids 1-274; SEQ ID NO: 1, or an amino acid 96-274 fragment of *mycoplasma* pneumonia P30 protein) but when the reaction is inhibited by the presence of protein B (domain III, or a fragment of domain III including at least one of the three amino acid repeating sequences (SEQ ID NOS: 3 to 5)) in an ELISA competitive inhibition test (competitive inhibition ELISA). The competitive inhibition ELISA in this definition may be a direct competition method, or an indirect competition method.

As an example of the indirect competition assay, 100 μL of 4 ng/mL of a full-length protein *mycoplasma* pneumonia P30 (amino acids 1-274; SEQ ID NO: 1) in 50 mM carbonate buffer (pH 9.5) is added to a 96-well ELISA plate Nunc Immuno modules (Thermo Fisher Scientific, Code 469949), and incubated at 4° C. for 16 hours. After the 16-hour incubation period, the P30 solution is removed, and the wells are washed three times with 300 μL of PBST (0.05% Tween 20 in PBS). The remaining solution in the wells is removed by tapping the plate against a paper towel.

Three-hundred microliters of a 5% BSA in PBST (BSA: Oriental Yeast Co., Ltd.) is added as a blocking solution, and incubated at 37° C. for 1 hour. After that, the BSA solution is removed, and the wells are washed three times with 300 μL of PBST (0.05% Tween 20 in PBS). The remaining solution in the wells is removed by tapping the plate against a paper towel, and full-length protein immobilized wells are obtained.

Thereafter, 100 μL of 5 μg/mL of anti-*Mycoplasma pneumoniae* P30 antibody (antibody P30(A)) in a 50% blocking solution is added as primary antibody to the full-length protein immobilized wells, and incubated at 37° C. for 1 hour. After that, the primary antibody solution is removed, and the wells are washed three times with 300 μL of PBST (0.05% Tween 20 in PBS).

Separately from the wells prepared by adding only the primary antibody, 100 μL of a 50% blocking solution containing 5 μg/mL of the primary antibody anti-*Mycoplasma pneumoniae* P30 antibody (antibody P30(A)), and the domain III or a fragment of domain III containing at least one of the three amino acid repeating sequences of the domain III (the domain III or the fragment being added in an amount 40 or 80 times the amount of the primary antibody) is added to wells, and incubated at 37° C. for 1 hour. After that, the primary antibody solution is removed, and the wells are washed three times with 300 μL of PBST (0.05% Tween 20 in PBS).

One-hundred microliters of 1 mg/mL of Anti Mouse IgG (H+L), Rabbit, IgG Whole, Peroxidase Cojugated (Wako Pure Chemical Industries, Ltd., Code 014-17611) is added as secondary antibody to the two types of wells prepared above, and incubated at 37° C. for 1.5 hours. After that, the BSA solution is removed, and the wells are washed three times with 300 μL of PBST (0.05% Tween 20 in PBS). The remaining solution in the wells is removed by tapping the plate against a paper towel.

One-hundred microliters of Sure Blue Reserve TMB Microwell Peroxidase Substrate (1-Component; KPL, Code 53-00-01) is added as a chromogenic substrate to the wells. A reaction is allowed for 15 minutes, and quenched by adding 100 μL of 2 N sulfuric acid.

Absorbance at 450 nm is measured using a microplate reader (BIORAD).

The antibody P30(A) "strongly recognizing domain III of P30 protein of *Mycoplasma pneumoniae*" can be confirmed when the absorbance of wells that contained both the primary antibody, and the domain III or a fragment of domain III containing at least one of the three amino acid repeating sequences of the domain III reduced from the absorbance of wells that contained only the primary antibody.

In the present invention, the antibody P30(A) can be said to strongly recognize domain III of P30 protein of *Mycoplasma pneumoniae* when the absorbance reduction is 30% or more in wells in which the domain III or a fragment of domain III containing at least one of the three amino acid repeating sequences of the domain III is used in 40 times the amount of the primary antibody, or when the absorbance reduction is 50% or more in wells in which the domain III or a fragment of domain III containing at least one of the three amino acid repeating sequences of the domain III is used in 80 times the amount of the primary antibody.

The antibody P30(A) used in the present invention may be, for example, a polyclonal antibody or a monoclonal antibody. For sensitivity, the antibody P30(A) is preferably a monoclonal antibody. The antibody P30(A) is available from, for example, Fucal Research under the trade name Mp-P30-3-AB.

An embodiment of the immunochromatographic analyzer of the present invention is described below with reference to the accompanying drawings. As used herein, the term "immobilized" means that the antibody is disposed on a support, such as a membrane, to prevent movement. The term "retain" as used herein means that the antibody is disposed so as to be movable in a support such as a membrane, or on a surface of the support.

In an embodiment, the immunochromatographic analyzer of the present invention is configured from a sample adding section (also referred to as "sample pad") (1), a label-substance retaining section (also referred to as "conjugate pad") (2), a chromatographic medium section (3), a detection section (4), an absorbing section (5), and a backing sheet (6), as illustrated in FIG. 1.

In the immunochromatographic analyzer, the sample adding section (1) is where an analyte-containing sample is added. The sample adding section (1), which quickly absorbs the sample, may be configured from a porous sheet of a property that allows a sample to smoothly move. Examples of such a porous sheet include cellulose filter paper, a glass fiber, polyurethane, polyacetate, cellulose acetate, nylon, and a cotton fabric.

The label-substance retaining section (2) contains a label substance (marker substance) to be described later. The label substance is retained in the label-substance retaining section (2) in the form of an antibody P30(A)-conjugated labeled antibody (hereinafter, also referred to simply as "labeled antibody"). The labeled antibody binds to the *Mycoplasma pneumoniae* in an analyte as the analyte moves in the label-substance retaining section. The label-substance retaining section (2) typically uses a membrane such as a glass fiber, and cellulose.

The labeled antibody content in the label-substance retaining section is typically 0.06 to 0.25 µg/analyzer, preferably 0.1 to 0.2 µg/analyzer, more preferably 0.1 to 0.15 µg/analyzer. The labeled antibody content per unit area of the label-substance retaining section is typically 0.1 to 0.42 µg/cm$^2$, preferably 0.17 to 0.33 µg/cm$^2$, more preferably 0.17 to 0.25 µg/cm$^2$.

Enzymes and the like are typically used for labeling of a detection reagent in immunochromatographic analysis. However, it is preferable to use an insoluble support as the label substance because it is suited for determining the presence of a target substance by visual inspection. A labeled detection reagent can be prepared by sensitizing the antibody P30(A) to the insoluble support. The antibody P30(A) may be sensitized to the insoluble support according to a known method.

The insoluble support as a label substance may be, for example, metal particles such as gold, silver, and platinum, metal oxide particles such as iron oxide, non-metallic particles such as sulfur, latex particles of synthetic high polymer, or any other insoluble support. The insoluble support is a label substance that is suited for visually determining the presence of a target substance, as described above, and is preferably colored to help make determination by visual inspection. Metal particles, and metal oxide particles have specific natural colors that vary with particle size, and the color may be used as a label.

Particularly preferred are gold particles because gold particles enable easy detection, and do not easily aggregate and produce non-specific colors. The gold particles should have an average particle size of, for example, 10 nm to 250 nm, preferably 35 nm to 120 nm. The average particle size can be calculated from the mean value of the measured diameters of the corresponding projected circle areas of arbitrarily selected 100 particles in a projected micrograph captured with a transmission electron microscope (TEM; JEOL, JEM-2010).

The gold particles contained in the label-substance retaining section are typically 0.25 to 0.7 µg/cm$^2$, preferably 0.3 to 0.65 µg/cm$^2$, more preferably 0.4 to 0.6 µg/cm$^2$ per unit area of the label-substance retaining section. In these ranges, the labeled particles can develop while being dispersed, and high sensitivity can be achieved without interfering with the antibody recognition sites.

The chromatographic medium section (3) is a development site of chromatography. The chromatographic medium section (3) is an inert membrane made of a fine porous substance that shows capillary action. The chromatographic medium section (3) is, for example, preferably a membrane made of nitrocellulose (hereinafter, also referred to as "nitrocellulose membrane"), or a membrane made of cellulose acetate (hereinafter, also referred to as "cellulose acetate membrane") because these materials are not reactive to the detection reagent, the immobilization reagent, or the target substance used in chromatography, and improve the effects of the present invention. A nitrocellulose membrane is more preferred. It is also possible to use cellulose membranes, nylon membranes, and porous plastic fabrics (polyethylene, polypropylene).

The nitrocellulose membrane may be a pure nitrocellulose membrane, or a mixed nitrocellulose membrane that is primarily nitrocellulose, as long as the main component is nitrocellulose.

The nitrocellulose membrane may contain a substance that promotes capillary action. Such a substance is preferably one that makes the membrane hydrophilic by lowering the surface tension of membrane. Preferred are amphiphatic substances that do not affect the movement of the target substance, or the color of the label substance. Examples of such substances include sugars, amino acid derivatives, fatty acid esters, various synthetic surfactants, and alcohols.

The nitrocellulose membrane is a porous membrane that shows capillary action. The index of capillary action can be checked by measuring capillary flow rate (capillary flow time). Capillary flow rate affects the detection sensitivity and the test time.

The form and size of the chromatographic medium section (3), which is typically a nitrocellulose membrane or a cellulose acetate membrane as described above, are not particularly limited, as long as the chromatographic medium section (3) has a form and a size that are appropriate in consideration of the actual procedures, and the observation of reaction results.

For easier procedures, it is preferable to provide a supporting member, such as a plastic, on the back surface of the chromatographic medium section (3). The properties of the supporting member are not particularly limited. However, for observation of measurement results by visual inspection, it is preferable to use a supporting member that has a color dissimilar to the color produced by the label substance. Preferably, the supporting member is typically colorless, or white.

The detection section (4) is formed on the chromatographic medium section (3). Specifically, the antibody P30 (A) that binds to the target substance *Mycoplasma pneumoniae* is immobilized at an arbitrarily selected location on the chromatographic medium section (3). The antibody P30(A) may be immobilized using an ordinary method.

The content of the antibody P30(A) in the detection section (4) is typically 0.1 to 2.5 µg/analyzer, preferably 0.3 to 2.0 µg/analyzer, more preferably 0.3 to 1.0 µg/analyzer. The content of the antibody P30(A) per unit area of the detection section (4) is typically 0.04 to 1.0 g/cm$^2$, preferably 0.125 to 0.8 µg/cm$^2$, more preferably 0.125 to 0.42 µg/cm$^2$.

The chromatographic medium section (3) may have a blocking treatment, as required, according to a known method, in order to prevent non-specific absorption that lowers the accuracy of analysis. Preferred as proteins used for the blocking treatment are typically bovine serum albumin, skim milk, casein, and gelatin. The blocking treatment may be followed by washing with one or more surfactants, for example, such as Tween 20, Triton X-100, and SDS, as needed.

The absorbing section (5) is provided at the end of the chromatographic medium section (3) to absorb the analyte, the developer, and other solutions that have passed the detection section (4). In the immunochromatographic analyzer of the present invention, the absorbing section (5) uses, for example, a nonwoven fabric such as a glass fiber, pulp, and a cellulose fiber, with or without containing a polymer such as an acrylic acid polymer, and a hydrophilic chemical having an ethylene oxide group or the like. Particularly preferred is a glass fiber. By using a glass fiber for the absorbing section (5), the return of the sample solution can be greatly reduced.

The backing sheet (6) is a base material. One side of the backing sheet (6) is made adhesive by applying an adhesive or attaching an adhesive tape. The sample adding section (1), the label-substance retaining section (2), the chromatographic medium section (3), the detection section (4), and the absorbing section (5) are attached to the adhesive surface, either in part or as a whole. The backing sheet (6) is not particularly limited, as long as it is a base material that, with an adhesive, is impermeable to the sample solution and is moisture impermeable.

The immunochromatographic analyzer fabricated in the manner described above is typically subjected to a drying treatment before being made into the final product. The drying temperature is, for example 20 to 50° C., and the drying time is 0.5 to 1 hour.

An immunochromatographic analysis kit of the present invention includes the immunochromatographic analyzer, and an analyte diluting solution for diluting and developing the analyte.

In the immunochromatographic analysis kit of the present invention, the analyte diluting solution is also usable as a developer. Typically, however, water is used as a solvent, and a buffer, a salt, and a non-ionic surfactant, and one or more components, for example, proteins, polymer compounds (such as PVP), ionic surfactants or polyanions, antimicrobial agents, and chelating agents for promoting antigen-antibody reaction or inhibiting non-specific reactions may be added to the solvent.

Particularly preferably, a non-ionic surfactant is contained in the analyte diluting solution to isolate P30 from the protein conjugates (P1, P90, P40, and P30) that are present in the cell adhesion part of *Mycoplasma pneumoniae*, and to expose the antigen recognition site of anti-P30 antibody. Examples of the non-ionic surfactant include Triton X-100 (trade name; polyethylene glycol mono-p-isooctylphenyl ether), Tween 20 (trade name; polyoxyethylene sorbitan monolaurate), NP-40 (the trade name; Nonidet 40), and Brij 35. These may be added alone or in a combination of two or more.

Preferably, at least 50% of the non-ionic surfactant contained in the analyte diluting solution is a non-ionic surfactant having an HLB value of 13 to 18. Further preferably, at least 60% of the non-ionic surfactant contained in the analyte diluting solution is a non-ionic surfactant having an HLB value of 13 to 17. Particularly preferably, 100% of the non-ionic surfactant contained in the analyte diluting solution is a non-ionic surfactant having an HLB value of 13 to 17. Specifically, it is preferable to contain Triton X-100 (HLB value: 13.7) and Tween 20 (HLB value: 16.7) in a 1:1 mass ratio.

When using the analyte diluting solution as a developer, the analyte and the developer may be mixed beforehand, and developed by supplying and dropping the mixture on the sample adding section. Alternatively, the developer may be developed by supplying and dropping on the sample adding section after supplying and dropping the analyte on the sample adding section.

An immunochromatographic analysis method of the present invention includes the following steps (1) to (4), and uses the immunochromatographic analyzer to detect the target substance *Mycoplasma pneumoniae* contained in an analyte.

(1) Step of adding to the sample adding section an analyte-containing solution prepared by diluting an analyte with an analyte diluting solution (2) Step of recognizing *Mycoplasma pneumoniae* with an antibody (hereinafter, "antibody P30(A)") that is retained in the label-substance retaining section, and that strongly recognizes domain III of P30 protein of *Mycoplasma pneumoniae* consisting of the amino acid sequence of SEQ ID NO: 2

(3) Step of developing the analyte and the antibody P30(A) as a mobile phase through the chromatographic medium section (4) Step of detecting the *Mycoplasma pneumoniae* in the mobile phase developed, using the antibody P30(A) contained in the detection section The following describes each step.

Step (1): Analyte-Containing Solution Prepared by Diluting an Analyte with Analyte Diluting Solution is Added to Sample Adding Section The analyte-containing solution in step (1) is preferably one prepared by adjusting or diluting the analyte with the analyte diluting solution to such a concentration that allows the analyte to smoothly move in the immunochromatography medium without lowering measurement accuracy. The analyte diluting solution may be those described above. A predetermined amount (typically, 0.1 to 2 mL) of the analyte-containing solution is dropped on the sample adding section (1). Upon being dropped, the analyte-containing solution starts moving in the sample adding section (1).

The analyte used in the present invention is an analyte that potentially contains the target substance *Mycoplasma pneumoniae*, and may be selected from biological samples, including, for example, a pharyngeal swab, a nasal swab, a nasal aspirate, a nasal wash, sputum, and an alveolar wash. However, the analyte is not limited to these.

Step (2): *Mycoplasma pneumoniae* is Recognized with an Antibody (hereinafter, "antibody P30(A)") that is Retained in the Label-Substance Retaining Section, and that Strongly Recognizes Domain III of P30 Protein of *Mycoplasma pneumoniae* Consisting of the Amino Acid Sequence of SEQ ID NO: 2

In step (2), the analyte-containing solution added to the sample adding section in step (1) is moved to the label-substance retaining section (2), and the domain III of P30 protein of the target substance *Mycoplasma pneumoniae* in the analyte is recognized by the label substance-conjugated antibody P30(A) retained in the label-substance retaining section.

The label substance may be those described above. The label substance-conjugated antibody P30(A) recognizes and binds to a part of the specific repeating sequences in the amino acid sequence of domain III of P30 protein.

Step (3): Analyte and Antibody P30(A) are Developed as Mobile Phase through Chromatographic Medium Section In step (3), the analyte and the antibody P30(A) are passed on the chromatographic medium section as a mobile phase after the label substance-conjugated antibody P30(A) has recognized the target substance *Mycoplasma pneumoniae* in the label-substance retaining section in step (2).

Step (4): *Mycoplasma pneumoniae* in the Mobile Phase is Detected Using the Antibody P30(A) Contained in Detection Section In step (4), the detection section produces a color after an antigen-antibody specific binding reaction in which the *Mycoplasma pneumoniae* in the analyte that has passed on the chromatographic medium section as a mobile phase specially reacts and binds by being sandwiched between the antibody P30(A) immobilized in the detection section and the antibody P30(A) conjugated to the label substance in step (2).

In step (4), the antibody P30(A) immobilized in the detection section forms a sandwich structure by binding to the same repeating sequence but at a different position from the sequence that has bound to the antibody P30(A) retained in the label-substance retaining section.

When the target substance *Mycoplasma pneumoniae* is absent, the labeled reagent dissolved in the moisture of a sample does not undergo a specific binding reaction even after passing the detection section on the chromatographic medium section, and does not produce a color in the detection section.

Finally, the moisture in the analyte-containing solution moves to the absorbing section (5).

EXAMPLES

The following describes the present invention in greater detail using Examples. The present invention, however, is not limited to the examples below.

Test Example 1

In this test, two different antibodies that recognize domain III of P30 protein of *Mycoplasma pneumoniae* were prepared, and the test examined whether these antibodies recognize which part of the domain III of P30 protein. The antibodies used are the antibodies Mp-P30-3-AB (hereinafter, "antibody P30(a)") and Mp-P30-9-AB (hereinafter, "antibody P30(b)") available from Fucal Research. The antibodies P30(a) and P30(b) were investigated for their binding sites on domain III of P30 protein of *Mycoplasma pneumoniae*, using the immunochromatographic analysis technique described below.

First, two peptides containing any of the three amino acid repeating sequences (SEQ ID NOS: 3 to 5) of domain III were created using an ordinary peptide chemical synthesis technique, specifically the solid-phase peptide synthesis technique.

```
Peptide 1:
                              (SEQ ID NO: 6)
PGMAPRPGMPPHPGMAPR

Peptide 2:
                              (SEQ ID NO: 7)
PGMAPRPGFPPQPGMAPR
```

The peptide 1 is a peptide having the amino acid sequence (PGMPPH) represented by SEQ ID NO: 4, and the amino acid sequence (PGMAPR) represented by SEQ ID NO: 3. The peptide 2 is a peptide having the amino acid sequence (PGFPPQ) represented by SEQ ID NO: 5, and the amino acid sequence (PGMAPR) represented by SEQ ID NO: 3.

The binding sites of the antibody P30(a) or P30(b) on domain III can be determined in the manner described below.

(1) Fabrication of Sample Adding Section

A glass-fiber nonwoven fabric (available from Millipore; 300 mm×30 mm) was used as the sample adding section.

(2) Fabrication of Label-Substance Retaining Section

The antibody P30(a) (the Fucal Research product Mp-P30-3-AB; 0.1 mL) that had been diluted with phosphate buffer (pH 7.4) to a concentration of 0.05 mg/mL was added to 0.5 mL of a gold colloidal suspension (Tanaka Kikinzoku Kogyo; LC 40 nm), and the mixture was allowed to stand at room temperature for 10 minutes.

Thereafter, 0.1 mL of a phosphate buffer (pH 7.4) containing 1 mass % bovine serum albumin (BSA) was added, and the mixture was allowed to stand at room temperature for 10 minutes. The mixture was thoroughly stirred, and centrifuged at 8,000×g for 15 minutes. After removing the supernatant, 0.1 mL of a phosphate buffer (pH 7.4) containing 1 mass % BSA was added. A label substance solution was obtained after these procedures.

A solution prepared by adding 300 μL of a 10 mass % trehalose aqueous solution and 1.8 mL of distilled water to 300 μL of the label substance solution prepared above was evenly added to a 12 mm×300 mm glass fiber pad (Millipore), and dried with a vacuum drier to obtain the label-substance retaining section.

(3) Fabrication of Chromatographic Medium Section and Detection Section

A nitrocellulose sheet (available from Millipore under the trade name HF120; 300 mm×25 mm) was used as a membrane.

Thereafter, 150 μL of a solution prepared by diluting the antibody P30(a) to a concentration of 1.0 mg/mL with a phosphate buffer (pH 7.4) containing 5 mass % isopropyl alcohol was linearly applied to the detection site (detection line) on the dried membrane in a width of 1 mm. Here, the solution was applied in an amount of 1 μL/mm (25 μL per sheet) using an immunochromatography dispenser XYZ3050 (BIODOT).

In order to confirm whether the gold particle-labeled reagent has developed or the rate of development, a solution of a goat-derived anti-serum having affinity to a wide range of gold particle-labeled substances, diluted with phosphate buffer (pH 7.4) was successively applied to the control site (control line) downstream of the detection site. The solution was dried at 50° C. for 30 minutes, and dried overnight at room temperature to obtain the chromatographic medium section and the detection section.

(4) Fabrication of Immunochromatographic Analyzer

The sample adding section, the label-substance retaining section, the chromatographic medium section having the detection section, and a glass-fiber nonwoven fabric used as the absorbing section for absorbing the developed sample and the label substance were attached to the backing sheet base material. This was cut to a width of 5 mm with a cutting machine to obtain the immunochromatographic analyzer. The label-substance retaining section had a length of 12 mm in the direction of sample development.

(5) Analyte Diluting Solution

A 50 mM HEPES buffer (pH 7.5) was prepared that contained a 1:1 mixture of a 1 mass % non-ionic surfactant NP-40 (available from Nacalai Tesque under the trade name Nonidet P-40; HLB value 17.7), and the NOF Corporation product Nonion MN-811 (HLB value 9.3). This solution was used as the analyte diluting solution for diluting an analyte.

(6) Measurement

The immunochromatographic analyzer fabricated in the manner described above was used with an analyte sample containing *Mycoplasma pneumoniae*, and peptide 1 or peptide 2, and the color intensity in the detection section was measured. A *mycoplasma* pneumonia P30 (purified protein P30Ag produced by expressing amino acids 96-274 with *Escherichia coli* using an ordinary method) was used as the analyte sample containing *Mycoplasma pneumoniae*. The P30Ag was adjusted to the desired concentration of 10 pg/mL with the foregoing extract. The peptide 1 or 2 contained in the analyte sample was prepared to have 400 ng of peptide 1 or peptide 2 develop.

The analyte sample (150 μL) was developed on the sample adding section of the immunochromatographic analyzer, and the extent of the produced color (color intensity) in the detection section was measured with a densitometer. (In the tables, the unit is mAbs.)

Determination When inhibited by peptide 1 and not inhibited by peptide 2, the antibody binds to the amino acid sequence (PGMPPH) represented by SEQ ID NO: 4.

When not inhibited by peptide 1 but inhibited by peptide 2, the antibody binds to the amino acid sequence (PGFPPQ) represented by SEQ ID NO: 5.

When inhibited by both peptide 1 and peptide 2, the antibody binds to the amino acid sequence (PGMAPR) represented by SEQ ID NO: 3.

A possible mechanism of the inhibition by the development of peptide 1 or peptide 2 with the analyte P30Ag is as follows. The peptide 1 and the peptide 2 have far smaller molecular weights than the analyte P30Ag, and are developed in much greater amounts than P30Ag. Accordingly, the peptides 1 and 2 reach the label-substance retaining section before P30Ag, and develop toward the detection section after binding to the antibody retained in the label-substance retaining section. However, because the peptides 1 and 2 have much fewer antibody binding sites (1 to 2 binding sites) than P30Ag, many of the peptide molecules that have bound to the antibody have only a few binding sites or no binding site for the antibody immobilized in the detection section. Many peptide molecules thus flow into the absorbing section without being captured in the detection section, with the result that the amount of the label substance that becomes captured and deposited in the detection section becomes smaller, and produces a weak color intensity. On the other hand, the antibody retained in the label-substance retaining section binds to the peptides 1 and 2 before binding to P30Ag, and the amount of the antibody that binds to the late-arriving P30Ag becomes smaller than when the peptide 1 or peptide 2 is absent. Accordingly, a large fraction of the P30Ag captured in the detection section is not conjugated to the antibody, and the color intensity due to the P30Ag detected in the detection section becomes weak as a result of inhibition.

In this test, an immunochromatographic analysis was conducted for the antibody P30(a) in three different experiments: without the peptide 1 or 2, with the peptide 1, and with the peptide 2. The results of color intensity measurements are presented in Table 1.

The results of the same experiments conducted for antibody P30(b) instead of antibody P30(a) are presented in Table 2.

TABLE 1

| Antibody P30(a) | | | |
|---|---|---|---|
| Peptide | None | Peptide 1 | Peptide 2 |
| Color intensity after 15 min (Abs) | 251.3 | 100.1 | 96.7 |

TABLE 2

| Antibody P30(b) | | | |
|---|---|---|---|
| Peptide | None | Peptide 1 | Peptide 2 |
| Color intensity after 15 min (Abs) | 58.2 | 60.9 | 31.3 |

As can be seen from the results shown in Table 1, the color intensity was weaker when the antibody P30(a) was used with peptide 1 and the color intensity was weaker when the antibody P30(a) was used with peptide 2 than when neither peptide was used. The results are suggestive of the antibody P30(a) being inhibited by both peptide 1 and peptide 2. From these results, the antibody P30(a) was shown to recognize the amino acid sequence (PGMAPR) represented by SEQ ID NO: 3.

From the results for antibody P30(b) shown in Table 2, it can be seen that the color intensity is the same without the peptides and with the peptide 1, but is weaker when the antibody P30(b) is used with peptide 2. The results suggest that the antibody P30(b) was inhibited by peptide 2, not by peptide 1. From these results, the antibody P30(b) was shown to recognize the amino acid sequence (PGFPPQ) represented by SEQ ID NO: 5.

Test Example 2

A test was conducted according to the ELISA described in paragraphs [0025] to [0030], and the competitive inhibition ELISA described in paragraphs [0032] to [0039] to confirm whether the antibody (antibody P30(a)) that recognizes domain III of P30 protein of *Mycoplasma pneumoniae* used in the immunochromatographic analyzer of the present invention produced in the Test Example 3 below is an antibody that "strongly" recognizes the domain III.

First, an ELISA was conducted according to the protocol described in paragraphs [0025] to [0030] to confirm whether the antibody P30(a) used in Test Example 1 is an antibody that strongly recognizes domain III of P30 protein of *Mycoplasma pneumoniae*. Specifically, the following experiment was conducted to find whether the antibody P30(a) has an absorbance at 450 nm of 0.2 Abs or more after subtracting the absorbance of a blank.

Firstly, 100 μL of 4 ng/mL of *mycoplasma* pneumonia P30 (purified protein P30Ag produced by expressing amino acids 96-274 with *Escherichia coli* using an ordinary method) in 50 mM carbonate buffer (pH 9.5) was added to a 96-well ELISA plate Nunc Immuno modules (Thermo Fisher Scientific, Code 469949), and incubated at 4° C. for 16 hours. After the 16-hour incubation period, the P30 solution was removed, and the wells are washed three times with 300 μL of PBST (0.05% Tween 20 in PBS). The remaining solution in the wells was removed by tapping the plate against a paper towel. Three-hundred microliters of a 5% BSA in PBST (BSA; Oriental Yeast Co., Ltd.) was added as a blocking solution, and incubated at 37° C. for 1 hour. After removing the BSA solution, the wells were washed three times with 300 μL of PBST (0.05% Tween 20 in PBS). The remaining solution in the wells was removed by tapping the plate against a paper towel.

One-hundred microliters of 5 μg/mL of the antibody P30(a) in 50% blocking solution (primary antibody solution) was added as primary antibody to the wells, and incubated at 37° C. for 1 hour. After removing the primary antibody solution, the wells were washed three times with 300 μL of PBST (0.05% Tween 20 in PBS). One-hundred microliters of 1 mg/mL of Anti Mouse IgG (H+L), Rabbit, IgG Whole, Peroxidase Cojugated (Wako Pure Chemical Industries, Ltd.; Code 014-17611) was added as secondary antibody to the wells, and incubated at 37° C. for 1.5 hours. After removing the BSA solution, the wells were washed three times with 300 μL of PBST (0.05% Tween 20 in PBS). The remaining solution in the wells was removed by tapping the plate against a paper towel.

One-hundred microliters of a chromogenic substrate Sure Blue Reserve TMB Microwell Peroxidase Substrate (1-Component; KPL; Code 53-00-01) was added to the wells. A reaction was allowed for 15 minutes, and quenched by adding 100 µL of 2 N sulfuric acid. Absorbance at 450 nm was measured using a microplate reader (BIORAD).

According to the foregoing method, the ELISA confirmed that the absorbance at 450 nm was 0.403 Abs, 0.2 Abs or more, after subtracting the absorbance of the blank (wells that underwent a chromogenic reaction with the secondary antibody without the primary antibody). That is, the test confirmed that the antibody P30(a) was an antibody that "strongly recognizes domain III of P30 protein of *Mycoplasma pneumoniae*".

In order to ascertain that the antibody P30(a) is an antibody that "strongly recognizes domain III of P30 protein of *Mycoplasma pneumoniae*", a competitive inhibition ELISA (indirect competition method) was conducted according to the protocol described in paragraphs [0032] to [0039]. Specifically, the following experiment was conducted to determine whether the absorbance shows a 30% or more reduction after the competitive inhibition ELISA using the antibody P30(a).

One-hundred microliters of 4 ng/mL of a full-length protein *mycoplasma* pneumonia P30 (amino acids 1-274; SEQ ID NO: 1) in 50 mM carbonate buffer (pH 9.5) was added to a 96-well ELISA plate Nunc Immuno modules (Thermo Fisher Scientific, Code 469949), and incubated at 4° C. for 16 hours. After the 16-hour incubation period, the P30 solution was removed, and the wells were washed three times with 300 μL of PBST (0.05% Tween 20 in PBS). The remaining solution in the wells was removed by tapping the plate against a paper towel.

Three-hundred microliters of a 5% BSA in PBST (BSA: Oriental Yeast Co., Ltd.) was added as a blocking solution, and incubated at 37° C. for 1 hour. After removing the BSA solution, the wells were washed three times with 300 μL of PBST (0.05% Tween 20 in PBS). The remaining solution in the wells was removed by tapping the plate against a paper towel, and full-length protein immobilized wells were obtained.

Thereafter, 100 μL of 5 μg/mL of anti-*Mycoplasma pneumoniae* P30 antibody (antibody P30(a)) in a 50% blocking solution was added as primary antibody to the full-length protein immobilized wells, and incubated at 37° C. for 1 hour. After removing the primary antibody solution, the wells were washed three times with 300 μL of PBST (0.05% Tween 20 in PBS).

Separately from the wells prepared by adding only the primary antibody, 100 μL of a 50% blocking solution containing 5 μg/mL of the primary antibody anti-*Mycoplasma pneumoniae* P30 antibody (antibody P30(a)), and the peptide 1 (SEQ ID NO: 6: PGMAPRPGMPPHPGMAPR) or the peptide 2 (SEQ ID NO: 7: PGMAPRPGFPPQPG-MAPR) used in Test Example 1 (the peptide 1 or peptide 2 being added in an amount 40 times the amount of the primary antibody) was added to wells, and incubated at 37° C. for 1 hour. After removing the primary antibody solution, the wells were washed three times with 300 μL of PBST (0.05% Tween 20 in PBS).

One-hundred microliters of 1 mg/mL of Anti Mouse IgG (H+L), Rabbit, IgG Whole, Peroxidase Cojugated (Wako Pure Chemical Industries, Ltd., Code 014-17611) was added as secondary antibody to the two types of wells prepared above, and incubated at 37° C. for 1.5 hours. After removing the BSA solution, the wells were washed three times with 300 μL of PBST (0.05% Tween 20 in PBS). The remaining solution in the wells was removed by tapping the plate against a paper towel.

One-hundred microliters of Sure Blue Reserve TMB Microwell Peroxidase Substrate (1-Component; KPL, Code 53-00-01) was added as a chromogenic substrate to the wells. A reaction was allowed for 15 minutes, and quenched by adding 100 μL of 2 N sulfuric acid.

Absorbance at 450 nm was measured using a microplate reader (BIORAD).

The test confirmed that the absorbance in the wells that contained the primary antibody and the peptide 1 or peptide 2 was at least 30% weaker than the absorbance observed in the wells that contained only the primary antibody. That is, it was confirmed that the antibody P30(a) "strongly recognizes domain III of P30 protein of *Mycoplasma pneumoniae*".

Test Example 3

Fabrication of Immunochromatographic Analyzer of the Present Invention

Example 1

(1) Fabrication of Sample Adding Section

A glass-fiber nonwoven fabric (available from Millipore; 300 mm×30 mm) was used as the sample adding section.

(2) Fabrication of Label-Substance Retaining Section

The antibody P30(a) (the Fucal Research product Mp-P30-3-AB; 0.1 mL) that had been diluted with phosphate buffer (pH 7.4) to a concentration of 0.05 mg/mL was added to 0.5 mL of a gold colloidal suspension (Tanaka Kikinzoku Kogyo; LC 40 nm), and the mixture was allowed to stand at room temperature for 10 minutes.

Thereafter, 0.1 mL of a phosphate buffer (pH 7.4) containing 1 mass % bovine serum albumin (BSA) was added, and the mixture was allowed to stand at room temperature for 10 minutes. The mixture was thoroughly stirred, and centrifuged at 8,000×g for 15 minutes. After removing the supernatant, 0.1 mL of a phosphate buffer (pH 7.4) containing 1 mass % BSA was added. A label substance solution was obtained after these procedures.

A solution prepared by adding 300 μL of a 10 mass % trehalose aqueous solution, and 1.8 mL of distilled water to 300 μL of the label substance solution prepared above was evenly added to a 12 mm×300 mm glass fiber pad (Millipore), and dried with a vacuum drier to obtain the label-substance retaining section.

(3) Fabrication of Chromatographic Medium Section and Detection Section

A nitrocellulose sheet (available from Millipore under the trade name HF120; 300 mm×25 mm) was used as a membrane.

Thereafter, 150 μL of a solution prepared by diluting the antibody P30(a) to a concentration of 1.0 mg/mL with a phosphate buffer (pH 7.4) containing 5 mass % isopropyl alcohol was linearly applied to the detection site (detection line) on the dried membrane in a width of 1 mm. Here, the solution was applied in an amount of 1 μL/mm (25 μL per sheet) using an immunochromatography dispenser XYZ3050 (BIODOT).

In order to confirm whether the gold particle-labeled reagent has developed or the rate of development, a solution of a goat-derived anti-serum having affinity to a wide range of gold particle-labeled substances, diluted with phosphate buffer (pH 7.4) was applied to the control site (control line) downstream of the detection site. The solution was dried at 50° C. for 30 minutes, and dried overnight at room temperature to obtain the chromatographic medium section and the detection section.

(4) Fabrication of Immunochromatographic Analyzer The sample adding section, the label-substance retaining section, the chromatographic medium section having the detection section, and a glass-fiber nonwoven fabric used as the absorbing section for absorbing the developed sample and the label substance were successively attached to the backing sheet base material. This was cut to a width of 5 mm with a cutting machine to obtain the immunochromatographic analyzer. The label-substance retaining section had a length of 12 mm in the direction of sample development.

(5) Analyte Diluting Solution

A 50 mM HEPES buffer (pH 7.5) was prepared that contained a 1:1 mixture of a 1 mass % non-ionic surfactant NP-40 (available from Nacalai Tesque under the trade name Nonidet P-40; HLB value 17.7), and the NOF Corporation product Nonidet MN-811 (HLB value 9.3). This solution was used as the analyte diluting solution for diluting an analyte.

(6) Measurement

The immunochromatographic analyzer fabricated in the manner described above was used with an analyte sample containing *Mycoplasma pneumoniae*, and the color intensity in the detection section was measured. A commercially available deactivated *Mycoplasma pneumoniae* (available from Meridian under the trade name *Mycoplasma pneumoniae* Antigen (FH)), or a pharyngeal swab from an individual infected with *mycoplasma* pneumonia was used as the analyte sample containing *Mycoplasma pneumoniae*. The pharyngeal swab was collected from two *mycoplasma* pneumonia-infected subjects by wiping the pharynx with a commercially available cotton swab.

The commercially available deactivated *Mycoplasma pneumoniae* was adjusted to the desired concentration with the foregoing extract, and used as the analyte sample ("Commercially available analyte" in Table 3).

The collected pharyngeal swab was used as the analyte sample after being diluted 20 times with the analyte diluting solution ("Subject 1" and "Subject 2" in Table 3).

The analyte samples (150 µL each) were developed on the sample adding section of the immunochromatographic analyzer, and the extent of the produced color (color intensity) in the detection section was measured with a densitometer. (In the tables, the unit is mAbs.) The results are presented in Table 3 and FIG. 2.

Comparative Example 1

Example 1 was repeated except that the antibody P30(a) in the antibody dilute solution applied to the detection section was replaced with the antibody P30(b) (the Fucal Research product Mp-P30-9-AB) used in Test Example 1. The results are presented in Table 3 and FIG. 2.

An ELISA was conducted as described in paragraphs [0025] to [0030], and a competitive inhibition ELISA was conducted as described in paragraphs [0032] to [0039] to confirm whether the antibody P30(b) "strongly recognizes domain III of P30 protein of *Mycoplasma pneumoniae*".

In order to confirm whether the antibody P30(b) is an antibody that strongly recognizes domain III of P30 protein of *Mycoplasma pneumoniae*, an ELISA was conducted according to the protocol described in paragraphs [0025] to [0030]. Specifically, the following experiment was conducted to determine whether the antibody P30(b) has an absorbance at 450 nm of 0.2 Abs or more after subtracting the absorbance of the blank.

One-hundred microliters of 4 ng/mL of *mycoplasma* pneumonia P30 (purified protein P30Ag produced by expressing amino acids 96-274 with *Escherichia coli* using an ordinary method) in 50 mM carbonate buffer (pH 9.5) was added to a 96-well ELISA plate Nunc Immuno modules (Thermo Fisher Scientific, Code 469949), and incubated at 4° C. for 16 hours. After the 16-hour incubation period, the P30 solution was removed, and the wells were washed three times with 300 µL of PBST (0.05% Tween 20 in PBS). The remaining solution in the wells was removed by tapping the plate against a paper towel. Three-hundred microliters of a 5% BSA in PBST (BSA; Oriental Yeast Co., Ltd.) was added as a blocking solution, and incubated at 37° C. for 1 hour. After removing the BSA solution, the wells were washed three times with 300 µL of PBST (0.05% Tween 20 in PBS). The remaining solution in the wells was removed by tapping the plate against a paper towel.

One-hundred microliters of 5 µg/mL of the antibody P30(b) in 50% blocking solution was added as primary antibody to the wells, and incubated at 37° C. for 1 hour. After removing the primary antibody solution antibody P30(b), the wells were washed three times with 300 µL of PBST (0.05% Tween 20 in PBS).

One-hundred microliters of 1 mg/mL of Anti Mouse IgG (H+L), Rabbit, IgG Whole, Peroxidase Cojugated (Wako Pure Chemical Industries, Ltd.; Code 014-17611) was added as secondary antibody to the wells, and incubated at 37° C. for 1.5 hours. After removing the BSA solution, the wells were washed three times with 300 µL of PBST (0.05% Tween 20 in PBS). The remaining solution in the wells was removed by tapping the plate against a paper towel.

One-hundred microliters of a chromogenic substrate Sure Blue Reserve TMB Microwell Peroxidase Substrate (1-Component; KPL; Code 53-00-01) was added to the wells. A reaction was allowed for 15 minutes, and quenched by adding 100 µL of 2 N sulfuric acid. Absorbance at 450 nm was measured using a microplate reader (BIORAD).

The ELISA confirmed that the absorbance at 450 nm was 0.061 Abs, less than 0.2 Abs, after subtracting the absorbance of the blank (wells that underwent a chromogenic reaction with the secondary antibody without the primary antibody). That is, the test confirmed that the antibody P30(b) was not an antibody that "strongly recognizes domain III of P30 protein of *Mycoplasma pneumoniae*".

In order to ascertain that the antibody P30(b) is an antibody that "strongly recognizes domain III of P30 protein of *Mycoplasma pneumoniae*", a competitive inhibition ELISA (indirect competition method) was conducted according to the protocol described in paragraphs [0032] to [0039]. Specifically, the following experiment was conducted to determine whether the reduced absorbance shows a 30% or less after the competitive inhibition ELISA.

One-hundred microliters of 10 ng/mL of a full-length protein *mycoplasma* pneumonia P30 (amino acids 1-274; SEQ ID NO: 1) in 50 mM carbonate buffer (pH 9.5) was added to a 96-well ELISA plate Nunc Immuno modules (Thermo Fisher Scientific, Code 469949), and incubated at 4° C. for 16 hours. After the 16-hour incubation period, the P30 solution was removed, and the wells were washed three times with 300 µL of PBST (0.05% Tween 20 in PBS). The remaining solution in the wells was removed by tapping the plate against a paper towel.

Three-hundred microliters of a 5% BSA in PBST (BSA: Oriental Yeast Co., Ltd.) was added as a blocking solution, and incubated at 37° C. for 1 hour. After removing the BSA solution, the wells were washed three times with 300 µL of PBST (0.05% Tween 20 in PBS). The remaining solution in the wells was removed by tapping the plate against a paper towel, and full-length protein immobilized wells were obtained.

Thereafter, 100 µL of 5 µg/mL of anti-*Mycoplasma pneumoniae* P30 antibody (antibody P30(b)) in a 50% blocking solution was added as primary antibody to the full-length protein immobilized wells, and incubated at 37° C. for 1 hour. After removing the primary antibody solution, the wells were washed three times with 300 µL of PBST (0.05% Tween 20 in PBS).

Separately from the wells prepared by adding only the primary antibody, 100 µL of a 50% blocking solution containing 5 µg/mL of the primary antibody anti-*Mycoplasma pneumoniae* P30 antibody (antibody P30(b)), and the peptide 1 (SEQ ID NO: 6: PGMAPRPGMPPHPG-MAPR) or the peptide 2 (SEQ ID NO: 7: PGMAPRPGFP-PQPGMAPR) used in Test Example 1 (the peptide 1 or peptide 2 being added in an amount 40 times the amount of the primary antibody P30(b)) was added to wells, and incubated at 37° C. for 1 hour. After removing the primary antibody solution, the wells were washed three times with 300 µL of PBST (0.05% Tween 20 in PBS).

One-hundred microliters of 1 mg/mL of Anti Mouse IgG (H+L), Rabbit, IgG Whole, Peroxidase Cojugated (Wako Pure Chemical Industries, Ltd., Code 014-17611) was added as secondary antibody to the two types of wells prepared above, and incubated at 37° C. for 1.5 hours. After removing the BSA solution, the wells were washed three times with 300 µL of PBST (0.05% Tween 20 in PBS). The remaining solution in the wells was removed by tapping the plate against a paper towel.

One-hundred microliters of Sure Blue Reserve TMB Microwell Peroxidase Substrate (1-Component; KPL, Code 53-00-01) was added as a chromogenic substrate to the wells. A reaction was allowed for 15 minutes, and quenched by adding 100 µL of 2 N sulfuric acid.

Absorbance at 450 nm was measured using a microplate reader (BIORAD).

The test confirmed that the absorbance in the wells that contained the primary antibody and the peptide 1 or peptide 2 showed no reduction with the peptide 1, and only an about 22% reduction with the peptide 2 from the absorbance observed in the wells that contained only the primary antibody. That is, the percentage reduction was less than 30%. In other words, the test showed that the antibody P30(b) was not an antibody that "strongly recognizes domain III of P30 protein of *Mycoplasma pneumoniae*".

Comparative Example 2

Example 1 was repeated except that the antibody P30(a) in the label substance solution added to the label-substance retaining section and the antibody P30(a) in the antibody dilute solution applied to the detection section were both replaced with the antibody P30(b). The results are presented in Table 3 and FIG. 2.

Comparative Example 3

Example 1 was repeated except that the antibody P30(a) in the antibody dilute solution applied to the detection section was replaced with an antibody against P1 protein of *Mycoplasma pneumoniae* (available from Meridian under the trade name MAb to *mycoplasma* pneumonia P1 (clone B1947M); hereinafter, referred to as "antibody P1(b)"). The results are presented in Table 3 and FIG. 2.

Comparative Example 4

Example 1 was repeated except that the antibody P30(a) in the label substance solution added to the label-substance retaining section was replaced with an antibody against P1 protein of *Mycoplasma pneumoniae* (available from Meridian under the trade name MAb to *mycoplasma* pneumonia P1 (clone B1948M); hereinafter, referred to as "antibody P1(a)"). The results are presented in Table 3 and FIG. 2.

Comparative Example 5

Example 1 was repeated except that the antibody P30(a) in the label substance solution added to the label-substance retaining section was replaced with the antibody P1(a), and that the antibody P30(a) in the antibody dilute solution applied to the detection section was replaced with the antibody P1(b). The results are presented in Table 3 and FIG. 2.

TABLE 3

| | | Ex. 1 | Com. Ex. 1 | Com. Ex. 2 | Com. Ex. 3 | Com. Ex. 4 | Com. Ex. 5 |
|---|---|---|---|---|---|---|---|
| Label-substance retaining section | | P30(a) | P30(a) | P30(b) | P30(a) | P1(a) | P1(a) |
| Detection section | | P30(a) | P30(b) | P30(b) | P1(b) | P30(a) | P1(b) |
| Color intensity (mAbs) | Commercially available analyte | 273 | 79.4 | 18.9 | 5.5 | 6.2 | 12.3 |
| | Subject 1 | 41.8 | 16.3 | 8.9 | 2.5 | 0 | 6.1 |
| | Subject 2 | 28.7 | 7.9 | 6.1 | 2.6 | 3 | 3 |

Example 2

Example 1 was repeated except that the composition of the analyte diluting solution was changed to Triton X-100 (trade name, Wako Pure Chemical Industries, Ltd.; polyethylene glycol mono-p-isooctylphenyl ether, HLB value: 13.7), and Tween 20 (trade name, Wako Pure Chemical Industries, Ltd.; polyoxyethylene sorbitan monolaurate, HLB value: 16.7). The results are presented in Table 4 and FIG. 3.

Comparative Example 6

Example 2 was repeated except that the antibody P30(a) in the antibody dilute solution applied to the detection section was replaced with the antibody P30(b). The results are presented in Table 4 and FIG. 3.

Comparative Example 7

Example 1 was repeated except that the antibody P30(a) in the label substance solution added to the label-substance retaining section, and the antibody P30(a) in the antibody dilute solution applied to the detection section were both replaced with the antibody P30(b). The results are presented in Table 4 and FIG. 3.

TABLE 4

|  |  | Ex. 2 | Com. Ex. 6 | Com. Ex. 7 |
|---|---|---|---|---|
| Label-substance retaining section | | P30(a) | P30(a) | P30(b) |
| Detection section | | P30(a) | P30(b) | P30(b) |
| Color intensity (mAbs) | Commercially available analyte | 490 | 159.2 | 40.5 |
| | Subject 1 | 117 | 29.8 | 15.2 |
| | Subject 2 | 51.7 | 13.6 | 8.9 |

Example 3

Example 1 was repeated except that the analyte was changed to P30 protein (purified protein P30Ag produced by expressing amino acids 96-274 with *Escherichia coli* using an ordinary method), and that the composition of the analyte diluting solution was changed to a 1:1 mixture of Triton X-100 (trade name, Wako Pure Chemical Industries, Ltd.; polyethylene glycol mono-p-isooctylphenyl ether, HLB value: 13.7), and Tween 20 (trade name, Wako Pure Chemical Industries, Ltd.; polyoxyethylene sorbitan monolaurate, HLB value: 16.7). The results are presented in Table 5 and FIG. 4.

Comparative Example 8

Example 3 was repeated except that the antibody P30(a) in the antibody dilute solution applied to the detection section was replaced with the antibody P30(b). The results are presented in Table 5 and FIG. 4.

Comparative Example 9

Example 3 was repeated except that the antibody P30(a) in the label substance solution added to the label-substance retaining section, and the antibody P30(a) in the antibody dilute solution applied to the detection section were both replaced with the antibody P30(b). The results are presented in Table 5 and FIG. 4.

Comparative Example 10

Example 3 was repeated except that the antibody P30(a) in the antibody dilute solution applied to the detection section was replaced with the antibody P1(b). The results are presented in Table 5 and FIG. 4.

Comparative Example 11

Example 3 was repeated except that the antibody P30(a) in the label substance solution added to the label-substance retaining section was replaced with the antibody P1(a). The results are presented in Table 5 and FIG. 4.

Comparative Example 12

Example 3 was repeated except that the antibody P30(a) in the label substance solution added to the label-substance retaining section was replaced with the antibody P1(a), and that the antibody P30(a) in the antibody dilute solution applied to the detection section was replaced with the antibody P1(b). The results are presented in Table 5 and FIG. 4.

TABLE 5

|  |  | Ex. 3 | Com. Ex. 8 | Com. Ex. 9 | Com. Ex. 10 | Com. Ex. 11 | Com. Ex. 12 |
|---|---|---|---|---|---|---|---|
| Label-substance retaining section | | P30(a) | P30(a) | P30(b) | P30(a) | P1(a) | P1(a) |
| Detection section | | P30(a) | P30(b) | P30(b) | P1(b) | P30(a) | P1(b) |
| Color intensity (mAbs) | P30Ag | 180 | 31.8 | 24.3 | 0 | 0 | 0 |

It was found from these results that the detection sensitivity to *Mycoplasma pneumoniae* or P30 protein greatly improves when the antibody P30(a) that strongly recognizes domain III of P30 protein of *Mycoplasma pneumoniae* was added to both the label-substance retaining section and the detection section (Examples 1 to 3), as compared with the other experiments (Comparative Examples 1 to 12).

Test Example 4

A competitive inhibition ELISA (indirect competition method) was conducted to confirm whether the antibody P30(a) of Test Example 2, and the antibody P30(b) of Comparative Example 1 are antibodies that "strongly recognize domain III of P30 protein of *Mycoplasma pneumoniae*". The competitive inhibition ELISA (indirect competition method) followed the procedures described in Test Example 2 or Comparative Example 1. The peptide 1 or peptide 2 used in Test Example 1 was used as the competitive fragment of domain III, and the peptide concentration was varied (×1 to ×640) as shown in the Tables 6 and 7 below. The results are presented in Tables 6 and 7. Table 6 shows the results for antibody P30(a). Table 7 shows the results for antibody P30(b). The results shown in Table 6 and Table 7 are represented in FIG. 5 and FIG. 6, respectively.

TABLE 6

| Peptide concentration (relative to the concentration of primary antibody anti-P30(a) antibody) | Color intensity (Abs) | | | | |
|---|---|---|---|---|---|
| | Competitive protein | | | | |
| | Peptide 1 | Percentage reduction of color intensity (%) | Peptide 2 | Percentage reduction of color intensity (%) | Control |
| 0 | 0.411 | — | 0.411 | — | 0.069 |
| ×1 | 0.37 | 10 | 0.401 | 2 | — |
| ×10 | 0.341 | 17 | 0.341 | 17 | — |
| ×20 | 0.322 | 22 | 0.29 | 29 | — |
| ×40 | 0.24 | 42 | 0.26 | 37 | — |
| ×80 | 0.17 | 59 | 0.199 | 52 | — |
| ×160 | 0.134 | 67 | 0.172 | 58 | — |
| ×320 | 0.132 | 68 | 0.16 | 61 | — |
| ×640 | 0.12 | 71 | 0.18 | 56 | — |

TABLE 7

| Peptide concentration (relative to the concentration of primary antibody anti-P30(b) antibody) | Color intensity (Abs) | | | |
|---|---|---|---|---|
| | Competitive protein | | | |
| | Peptide 1 | Peptide 2 | Percentage reduction of color intensity (%) | Control |
| 0 | 0.208 | 0.208 | — | 0.069 |
| ×1 | 0.226 | 0.199 | 4 | — |
| ×10 | 0.256 | 0.184 | 12 | — |
| ×20 | 0.228 | 0.186 | 11 | — |
| ×40 | 0.232 | 0.163 | 22 | — |
| ×80 | 0.237 | 0.133 | 36 | — |
| ×160 | 0.223 | 0.125 | 40 | — |
| ×320 | 0.23 | 0.11 | 47 | — |
| ×640 | 0.225 | 0.114 | 45 | — |

As can be seen in the results shown in Table 6 and FIG. 5, a 30% or more reduction was confirmed in the absorbance of the wells relative to the control when the peptide concentration was higher than the primary antibody anti-P30(a) antibody concentration by a factor of 40. The percentage reduction was 50% or more with a peptide concentration 80 times the antibody concentration. From the result that the antibody P30(a) was inhibited by both peptide 1 and peptide 2, the antibody P30(a) was shown to recognize the amino acid sequence (PGMAPR) represented by SEQ ID NO: 3.

From the results shown in Table 7 and FIG. 6, the percentage reduction of well absorbance was only about 22%, less than 30%, relative to the control, when the peptide concentration was 40 times the concentration of the primary antibody P30(b). That is, it was confirmed that the antibody P30(b) was not an antibody that "strongly recognizes domain III of P30 protein of *Mycoplasma pneumoniae*". From the result that the antibody P30(b) was inhibited by peptide 2 and not by peptide 1, the antibody P30(b) was shown to recognize the amino acid sequence (PGFPPQ) represented by SEQ ID NO: 5.

While there has been described a certain embodiment of the invention in detail, it will be understood by a skilled person that various changes and modifications may be made thereto without departing from the spirit and scope of the invention. This patent application is based on Japanese patent application (No. 2015-111732) filed Jun. 1, 2015, and Japanese patent application (No. 2015-171163) filed Aug. 31, 2015, the entire contents of which are hereby incorporated by reference.

INDUSTRIAL APPLICABILITY

The present invention enables a quick and easy, high-sensitivity detection of *Mycoplasma pneumoniae* with the immunochromatographic analyzer that uses an antibody that binds to a specific site of P30 protein of *Mycoplasma pneumoniae*. The invention has use in early diagnosis of mycoplasma pneumonia.

REFERENCE SIGNS LIST

1: Sample adding section (sample pad)
2: Label-substance retaining section
3: Chromatographic medium section
4: Detection section
5: Absorbing section
6: Backing sheet

The invention claimed is:

1. An immunochromatographic kit comprising: an immunochromatographic analyzer for detecting *Mycoplasma pneumoniae* and an analyte diluting solution for diluting and developing an analyte, wherein the immunochromatographic analyzer comprises:
- a sample adding section;
- a label-substance retaining section;
- a chromatographic medium section having a detection section; and
- an absorbing section,
wherein the label-substance retaining section and the detection section contain an antibody that recognizes the amino acid sequence of SEQ ID NO: 3 in domain III of the P30 protein of *Mycoplasma pneumoniae* consisting of the amino acid sequence of SEQ ID NO: 2, and
wherein the content of the antibody in the label-substance retaining section is 0.06 to 0.25 μg/device, and the analyte diluting solution contains a non-ionic surfactant having a hydrophilic-lipophilic balance value of 13 to 17.

2. The immunochromatographic analyzer according to claim 1, wherein the label substance contained in the label-substance retaining section is a gold particle, and the label-substance retaining section contains the gold particle in an amount of 0.25 to 0.7 μg/cm2.

3. The immunochromatographic analysis kit according to claim 1, wherein the analyte diluting solution contains one or more non-ionic surfactants and at least 50% of the non-ionic surfactant contained in the analyte diluting solution is the non-ionic surfactant having a hydrophilic-lipophilic balance value of 13 to 17.

4. A method for detecting *Mycoplasma pneumoniae* in an analyte using an immunochromatographic analyzer that includes a sample adding section, a label-substance retaining section, a chromatographic medium section having a detection section and an absorbing section, the method comprising the steps of:
(1) adding to the sample adding section an analyte-containing solution prepared by diluting the analyte with an analyte diluting solution;
(2) recognizing *Mycoplasma pneumoniae* with an antibody (hereinafter, "antibody P30(A)") that is retained in the label-substance retaining section, and that recognizes the amino acid sequence of SEQ ID NO: 3 in domain III of the P30 protein of *Mycoplasma pneumoniae* consisting of the amino acid sequence of SEQ ID NO: 2;
(3) developing the analyte and the antibody P30(A) as a mobile phase through the chromatographic medium section; and
(4) detecting the *Mycoplasma pneumoniae* in the mobile phase developed, using the antibody P30(A) contained in the detection section.

* * * * *

SEQUENCE LISTING

<160> NUMBER OF SEQ ID NOS: 7

<210> SEQ ID NO 1
<211> LENGTH: 274
<212> TYPE: PRT
<213> ORGANISM: Mycoplasma pneumoniae

<400> SEQUENCE: 1

Met Lys Leu Pro Pro Arg Arg Lys Leu Lys Leu Phe Leu Leu Ala Trp
1               5                   10                  15

```
Met Leu Val Leu Phe Ser Ala Leu Ile Val Leu Ala Thr Leu Ile Leu
            20                  25                  30

Val Gln His Asn Asn Thr Glu Leu Thr Glu Val Lys Ser Glu Leu Ser
        35                  40                  45

Pro Leu Asn Val Val Leu His Ala Glu Glu Asp Thr Val Gln Ile Gln
    50                  55                  60

Gly Lys Pro Ile Thr Glu Gln Ala Trp Phe Ile Pro Thr Val Ala Val
65                  70                  75                  80

Cys Phe Gly Phe Ser Ala Leu Ala Ile Ile Leu Gly Leu Ala Ile Gly
                85                  90                  95

Leu Pro Ile Val Lys Arg Lys Glu Lys Arg Leu Leu Glu Glu Lys Glu
            100                 105                 110

Arg Gln Glu Gln Leu Ala Glu Gln Leu Gln Arg Ile Ser Ala Gln Gln
        115                 120                 125

Glu Glu Gln Gln Ala Leu Gln Gln Ala Ala Glu Ala His Ala
    130                 135                 140

Glu Ala Glu Val Glu Pro Ala Pro Gln Pro Val Pro Val Pro Pro Gln
145                 150                 155                 160

Pro Gln Val Gln Ile Asn Phe Gly Pro Arg Thr Gly Phe Pro Pro Gln
                165                 170                 175

Pro Gly Met Ala Pro Arg Pro Gly Met Pro Pro His Pro Gly Met Ala
            180                 185                 190

Pro Arg Pro Gly Phe Pro Pro Gln Pro Gly Met Ala Pro Arg Pro Gly
        195                 200                 205

Met Pro Pro His Pro Gly Met Ala Pro Arg Pro Gly Phe Pro Pro Gln
    210                 215                 220

Pro Gly Met Ala Pro Arg Pro Gly Met Pro Pro His Pro Gly Met Ala
225                 230                 235                 240

Pro Arg Pro Gly Phe Pro Pro Gln Pro Gly Met Ala Pro Arg Pro Gly
                245                 250                 255

Met Gln Pro Pro Arg Pro Gly Met Pro Pro Gln Pro Gly Phe Pro Pro
            260                 265                 270

Lys Arg

<210> SEQ ID NO 2
<211> LENGTH: 98
<212> TYPE: PRT
<213> ORGANISM: Mycoplasma pneumoniae

<400> SEQUENCE: 2

Pro Gly Met Ala Pro Arg Pro Gly Met Pro Pro His Pro Gly Met Ala
1               5                   10                  15

Pro Arg Pro Gly Phe Pro Pro Gln Pro Gly Met Ala Pro Arg Pro Gly
            20                  25                  30

Met Pro Pro His Pro Gly Met Ala Pro Arg Pro Gly Phe Pro Pro Gln
        35                  40                  45

Pro Gly Met Ala Pro Arg Pro Gly Met Pro Pro His Pro Gly Met Ala
    50                  55                  60

Pro Arg Pro Gly Phe Pro Pro Gln Pro Gly Met Ala Pro Arg Pro Gly
65                  70                  75                  80

Met Gln Pro Pro Arg Pro Gly Met Pro Pro Gln Pro Gly Phe Pro Pro
                85                  90                  95

Lys Arg
```

```
<210> SEQ ID NO 3
<211> LENGTH: 6
<212> TYPE: PRT
<213> ORGANISM: Mycoplasma pneumoniae P30

<400> SEQUENCE: 3

Pro Gly Met Ala Pro Arg
1               5

<210> SEQ ID NO 4
<211> LENGTH: 6
<212> TYPE: PRT
<213> ORGANISM: Mycoplasma pneumoniae P30

<400> SEQUENCE: 4

Pro Gly Met Pro Pro His
1               5

<210> SEQ ID NO 5
<211> LENGTH: 6
<212> TYPE: PRT
<213> ORGANISM: Mycoplasma pneumoniae P30

<400> SEQUENCE: 5

Pro Gly Phe Pro Pro Gln
1               5

<210> SEQ ID NO 6
<211> LENGTH: 18
<212> TYPE: PRT
<213> ORGANISM: Mycoplasma pneumoniae P30

<400> SEQUENCE: 6

Pro Gly Met Ala Pro Arg Pro Gly Met Pro Pro His Pro Gly Met Ala
1               5                   10                  15

Pro Arg

<210> SEQ ID NO 7
<211> LENGTH: 18
<212> TYPE: PRT
<213> ORGANISM: Mycoplasma pneumoniae P30

<400> SEQUENCE: 7

Pro Gly Met Ala Pro Arg Pro Gly Phe Pro Pro Gln Pro Gly Met Ala
1               5                   10                  15

Pro Arg
```